United States Patent
Larsson et al.

(10) Patent No.: US 9,370,636 B2
(45) Date of Patent: Jun. 21, 2016

(54) ANESTHETIC VAPORIZER FOR A BREATHING APPARATUS AND METHOD FOR OPERATION THEREOF TO VAPORIZE A LIQUID ANESTHETIC AGENT

(75) Inventors: Åke Larsson, Järfälla (SE); Carl Troili, Danderyd (SE)

(73) Assignee: Maquet Critical Care AB, Solna (SE)

( * ) Notice: Subject to any disclaimer, the term of this patent is extended or adjusted under 35 U.S.C. 154(b) by 438 days.

(21) Appl. No.: 13/997,407

(22) PCT Filed: Dec. 22, 2010

(86) PCT No.: PCT/EP2010/070614
§ 371 (c)(1),
(2), (4) Date: Jun. 24, 2013

(87) PCT Pub. No.: WO2012/084042
PCT Pub. Date: Jun. 28, 2012

(65) Prior Publication Data
US 2013/0276782 A1    Oct. 24, 2013

(51) Int. Cl.
*A61M 11/00* (2006.01)
*A61M 16/18* (2006.01)
*A61M 16/10* (2006.01)

(52) U.S. Cl.
CPC .......... *A61M 16/18* (2013.01); *A61M 16/1075* (2013.01); *A61M 2205/3368* (2013.01); *A61M 2205/3646* (2013.01)

(58) Field of Classification Search
CPC ..... A61M 16/16; A61M 16/18; A61M 16/20; A61M 16/104; A61M 16/1045; A61M 16/1075; A61M 2205/3368; A61M 2205/3646

USPC .......... 128/203.14, 203.26, 203.27; 261/128, 261/130
See application file for complete search history.

(56) References Cited

U.S. PATENT DOCUMENTS

| 2003/0131844 | A1 | 7/2003 | Kumar et al. |
| 2006/0037613 | A1 | 2/2006 | Kwok et al. |
| 2015/0014874 | A1* | 1/2015 | Winski ............... A61M 16/0051 261/128 |
| 2015/0209546 | A1* | 7/2015 | Pernikoff ............. A61M 16/01 128/202.27 |

FOREIGN PATENT DOCUMENTS

WO    2008145177 A1    12/2008

* cited by examiner

*Primary Examiner* — Steven Douglas
(74) *Attorney, Agent, or Firm* — Schiff Hardin LLP (57) ABSTRACT

In an anesthesia vaporizer for vaporizing an anesthetic agent liquid and a method of vaporizing an anesthetic agent liquid in an vaporizer, an evaporation unit evaporates the anesthetic agent, a delivery unit intermittently adds a volume of said liquid to the evaporation unit in order to evaporate at least a portion of the volume of the liquid from the evaporation unit. A heat energy storage unit includes a phase change material (PCM) and is thermally coupled to at least a portion of the evaporation unit. The PCM has a phase shift temperature that is higher than the evaporation temperature of the anesthetic agent. The PCM in the heat energy storage unit is preferably at least partly liquid at an operative temperature of the vaporizer.

26 Claims, 4 Drawing Sheets

ANESTHETIC VAPORIZER FOR A BREATHING APPARATUS AND METHOD FOR OPERATION THEREOF TO VAPORIZE A LIQUID ANESTHETIC AGENT

BACKGROUND OF THE INVENTION

1. Field of the Invention

This invention pertains in general to the field of vaporizing devices and methods for breathing apparatuses, in particular anesthetic vaporizers. More particularly the invention relates to an anesthesia injection vaporizer device and method for vaporizing a liquid anesthetic agent in a breathing apparatus.

2. Description of the Prior Art

German published patent application number DE4105370 of Drägerwerk AG, published in 1992, discloses an anesthetic vaporizer device. The vaporizer is of the evaporation vaporizer type, as disclosed in German published patent application number DE1271903. A liquid anesthetic agent is stored in a vessel. The liquid anesthetic agent is drawn up by a cylindrical wick. Air becomes saturated with the anesthetic agent by flowing past the wick. The liquid is kept at a constant low temperature by a latent heat storage device to avoid unintentional evaporation. This is in particular applicable to liquids having low evaporation temperatures around room temperature, such as Desflurane. The latent heat storage device disclosed in DE4105370 is arranged in the evaporation vaporizer to keep the temperature of the anesthetic vaporizer device constant, namely at a temperature lower than the evaporation temperature of the anesthetic agent.

In more detail, the anesthetic vaporizer disclosed in DE4105370 device consists of an outer vessel with double walls and with the space between the walls being filled with thermal insulation. The outer vessel is filled with a material, such as a wax, which melts at the same temperature as the required storage temperature of the liquid anesthetic agent. It should be observed that a storage temperature for an anesthetic agent liquid is substantially lower than its boiling point or evaporation temperature. Any change in ambient temperature causes the wax to melt or solidify so that the wax gains or releases latent heat without any change in the temperature of the wax. The wax is thus merely arranged as a heat buffer, improving isolation of a large volume of the liquid anesthetic agent inside a container of the evaporation vaporizer in relation to temperature changes of the environment surrounding the evaporation vaporizer.

Since 1992 development of anesthetic vaporizers has advanced considerably. Injection principle based vaporizers have been developed, and the devices are commonly known as injection vaporizers.

In a modern injection vaporizer injecting a liquid anesthetic agent for evaporation purposes, requirements are very high regarding the quickness of the vaporization process. An injection vaporizer injects or sprays intermittently a pulse of a small amount of the anesthetic agent liquid into a vaporizing chamber or a channel by means of an atomizing technique. A spray of droplets of the liquid is generated by the injection. The liquid is thus gasified into a flow of a carrier gas, often a mixture of nitrous oxide or air and oxygen. The mean flow of the liquid is controlled by the time length of a pulse and the frequency of pulses. Typically, such dosing pulses have a duration between 2 to 10 msec.

The vaporization rate of the droplets in turn depends on the amount of heat energy available for providing the transformation from the liquid phase to the gaseous phase of the anesthetic agent. It depends further on the removal rate of the gaseous medium from the surface of the liquid droplet to keep the vaporizing process ongoing until the droplet is completely gasified.

Known injection vaporizers are based on a temperature regulation of the temperature of the vaporization chamber that only control the mean temperature therein in a slow process. Temperature regulation can thus not follow the quick injection process and related vaporization events following the aforementioned extremely short injection pulses.

The power that would be needed to provide the heat energy necessary to instantly gasify injected liquid is in the range of approximately 60 to 80 Watts. However, such high power is not available at the vaporization site. In addition, breathing apparatuses in which the injection vaporizers are used, have limited effect available due to safety requirements concerning battery backup drift, limiting available power.

Moreover, temperature regulation is slow as feedback is thermistor based. The thermistor has a time constant of several seconds and temperature regulation thus in the range of Hz. This allows only for a correspondingly slow temperature regulation process of the mean temperature in the vaporization chamber.

Vaporization in an injector vaporizer thus takes place in two stages. A minor portion of the liquid gasifies during the flight from the injector towards an interior wall of a vaporizer chamber in the injection vaporizer unit. The major portion of the injected liquid is gasified in a secondary stage from the wall of the vaporizer chamber.

However, due to a low thermal capacity of the volume available for the vaporization process, temperature drops quickly in the vaporization chamber following the injection pulse. This temperature drop may lead to such low temperatures that the vaporization of the liquid injected anesthetic agent ceases. This would be undesired in clinical operation The latent heat storage device of DE4105370 is arranged to keep the entire vaporizer device at a constant temperature below the vaporization temperature and is furthermore not suitable to compensate for such quick, locally occurring temperature changes inside a vaporizing chamber of modern injection vaporizers.

Thus, there is a need for an improved injection vaporizer. The improved injection vaporizer should advantageously provide effective vaporization.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing an anesthetic vaporizer, preferably an injection vaporizer, and a method of vaporizing an anesthetic agent liquid in an injection vaporizer, according to the appended patent claims.

Embodiments of the invention provide for sufficient heat (or thermal) energy being available for reliably vaporizing, i.e. gasifying, the liquid that lands on a surface of the injection vaporizer when injected. The supply of necessary evaporation heat energy, that might not be provided form a heater element only, as explained above, is provideable by means of a phase change material (PCM). The PCM is arranged in a heat energy storage unit. The PCM provides for avoiding local temperature drops by locally bridging the delivery of evaporation heat at the surface where the liquid has landed. The PCM is thermally coupled to the surface. By providing a PCM that has a melting temperature above the evaporation temperature of the anesthetic agent, it is ensured that the temperature of the surface is permanently above the evaporation temperature. The term "evaporation temperature" in the present context is a desired temperature at which an anesthetic agent liquid evaporates, such as during operation of an anesthetic vaporizer. The evaporation temperature, or the boiling point, is for instance pressure dependent, but is lower at higher pressures than standard sea level atmospheric pressure. The PCM is chosen to have a phase shift temperature that exceeds a maximum evaporation temperature of a respective anesthetic agent in operative conditions of the anesthetic vaporizer.

Thus evaporation is facilitated. Evaporation is provided in a reliable manner. Thermal energy stored in the PCM of a heat energy storage unit provides for temperature stabilization during intermittent injection evaporation. Thermal Energy is provided as a cyclic, temporary storage of high temperature energy. The high temperature energy is provided to charge a PCM to the high temperature at least during time slots where no evaporation occurs. Thermal input energy may also be provided continuously to the PCM, i.e. also during evaporation. Thermal input energy provided to the PCM is usually provided in form of electrical energy converted to heat energy in a heater unit. The input energy is however lower than the peak thermal energy provideable thanks to the PCM from previous thermal charging thereof. In this manner, the PCM is provided to bridge a time gap between energy requirement and energy use. This has a number of advantages, including smaller heater units and/or smaller, cheaper injector vaporizers. Moreover, accumulation of liquid in the injection vaporizer is effectively prevented and evaporation of anesthetic agents is reliably provided.

In more detail, when a pulse of the injected liquid lands on the surface of a vaporization chamber or channel, the vaporization starts immediately. The temperature would now locally drop at the landing surface as the phase shift of the liquid anesthetic agent to the gasified anesthetic agent requires an amount of evaporation heat supplied by the surface. However, the PCM prevents a temperature drop below a phase shift temperature of the PCM, which is above the vaporization temperature of the anesthetic agent. Evaporation is thus continued rather than prevented as conventionally by the temperature drop. The thermal resistance between the PCM and the liquid on the surface is minimized. Thus the temperature may drop locally at the surface during evaporation, but will stay at a constant level at the phase shift temperature of the PCM. The PCM may solidify partly, but the amount of PCM is dimensioned that it will not entirely solidify until all liquid from an injected pulse is gasified. During a pause until the next injection pulse, the PCM is entirely liquefied again and the temperature of the PCM may be raised over the melting/solidification temperature to store sufficient heat energy for the next injected liquid pulse.

A global, slow temperature regulation controls the medium temperature so that the PCM is kept at a sufficient high temperature. By locally applying small amounts of PCM, heating energy needed for a reliable injection vaporizer is kept low.

The PCM is in thermal contact with the evaporation surface. Transmission of heat from the PCM to the evaporation surface may be made by direct contact of the two latter. Alternatively, the PCM may be arranged at a distance from the evaporation surface and thermal contact is established by means of thermally conductive elements. Thermally conductive elements may be provided in form of heat pipes or heat sinks suitably arranged.

According to a first aspect of the invention, an anesthesia vaporizer is provided. The vaporizer is provided for vaporizing an anesthetic agent liquid into a gaseous phase. The vaporizer is preferably used in a breathing apparatus for anesthesia purposes. Generally, a level of anesthesia, such as induced by intra venous administration of anesthetic pharmaceuticals, is maintained by administration of a gasified anesthetic agent with breathing gases to the patient. The vaporizer comprises an evaporation unit for evaporating the anesthetic agent. Further, it has a delivery unit for intermittently adding a volume of the liquid to the evaporation unit for evaporating at least a portion of the volume of the liquid from the evaporation unit. Moreover, the vaporizer includes a heat energy storage unit including a phase change material (PCM). The heat energy storage unit is arranged such that it is thermally coupled to the evaporation unit. Further, the PCM has a phase shift temperature that is higher than the evaporation temperature of the anesthetic agent.

In embodiments, the PCM in the heat energy storage unit is at least partly liquid at an operative temperature of the vaporizer.

Preferably, the delivery unit is an injection unit and the vaporizer thus an injection vaporizer. In embodiments, the injecting unit is provided for generating a pulsed, intermittent spray of the liquid towards the evaporation surface portion for evaporating the injected liquid at least partly from the evaporation surface.

In some embodiments, the vaporizer has a gas flow channel including a vaporizer chamber. A gas flow passing through the gas flow channel is enriched with the evaporated anesthetic agent during operation of the injection vaporizer in a breathing apparatus.

Preferably, the evaporation unit is arranged in the vaporizer chamber as at least a portion of an interior evaporation surface thereof. In such embodiments, the heat energy storage unit comprising the PCM is thermally coupled to the evaporation surface.

In some embodiments the vaporizer comprises an interior evaporation surface portion. An injecting unit is for instance provided for generating a pulsed, intermittent spray of the liquid towards the evaporation surface portion for evaporating the injected liquid at least partly from the evaporation surface when landing thereon. Further, a heat energy storage unit comprises a phase change material (PCM). The heat energy storage unit is thermally coupled to at least a portion of the evaporation surface. The PCM arranged in the heat energy storage unit has a phase shift temperature that is higher than the evaporation temperature of the anesthetic agent. In this manner the PCM is provided at least partly liquid at an operative temperature of the vaporizer. Vaporization is thus advantageously improved. Temperature at an evaporation surface is stabilized at a level above the evaporation temperature of the liquid.

According to a second aspect of the invention, a method of vaporizing an anesthetic agent liquid in an anesthetic vaporizer is provided. The method comprises providing a heat energy storage unit comprising a phase change material (PCM), which heat energy storage unit is thermally coupled to at least a portion of an evaporation unit. Further, the method has a step of intermittently adding a volume of the liquid from a delivery unit to the evaporation unit. Moreover, the method includes a step of evaporating at least a portion of the volume of the liquid from the evaporation unit. The PCM has a phase shift temperature, such as a solidification temperature or liquefaction temperature, which is higher than the evaporation temperature of the anesthetic agent. Thus the method provides for stabilizing a temperature of the evaporation unit during the evaporating.

Preferably, the method includes the step of keeping the PCM in the heat energy storage unit at least partly liquid at an operative temperature of the vaporizer.

Preferably, the step of adding a volume includes injecting a volume of the liquid in the injection vaporizer. This is preferably done into a gas flow channel or a vaporizer chamber including the gas flow channel. The evaporation unit is arranged in the vaporizer chamber as an interior evaporation surface thereof. The heat energy storage unit includes the phase change material (PCM) thermally coupled to at least a portion of the evaporation surface. In some embodiments, the method includes the step of injecting a pulsed, intermittent spray of the liquid towards the evaporation surface portion, and the method comprises evaporating the injected liquid at least partly from the evaporation surface.

In particular, the method includes the step of stabilizing a temperature of the evaporation surface portion during the evaporation by heat provided by the PCM. This may include instantaneously providing heat energy from the PCM to the evaporation surface portion and thus the liquid for continued evaporation upon delivery, such as injection of the spray, into a vaporization chamber of the vaporizer.

Preferably, the method includes the step of storing the liquid in a container arranged remote from a vaporization chamber of the vaporizer, and conveying the liquid to the evaporation unit. This may include conveying the liquid to an injection unit of the injection vaporizer for generating the pulsed, intermittent spray of the liquid. Alternatively, or in addition, a pump, such as a micropump, may be provided for conveying the liquid into the vaporization chamber for evaporation.

Figure 1:
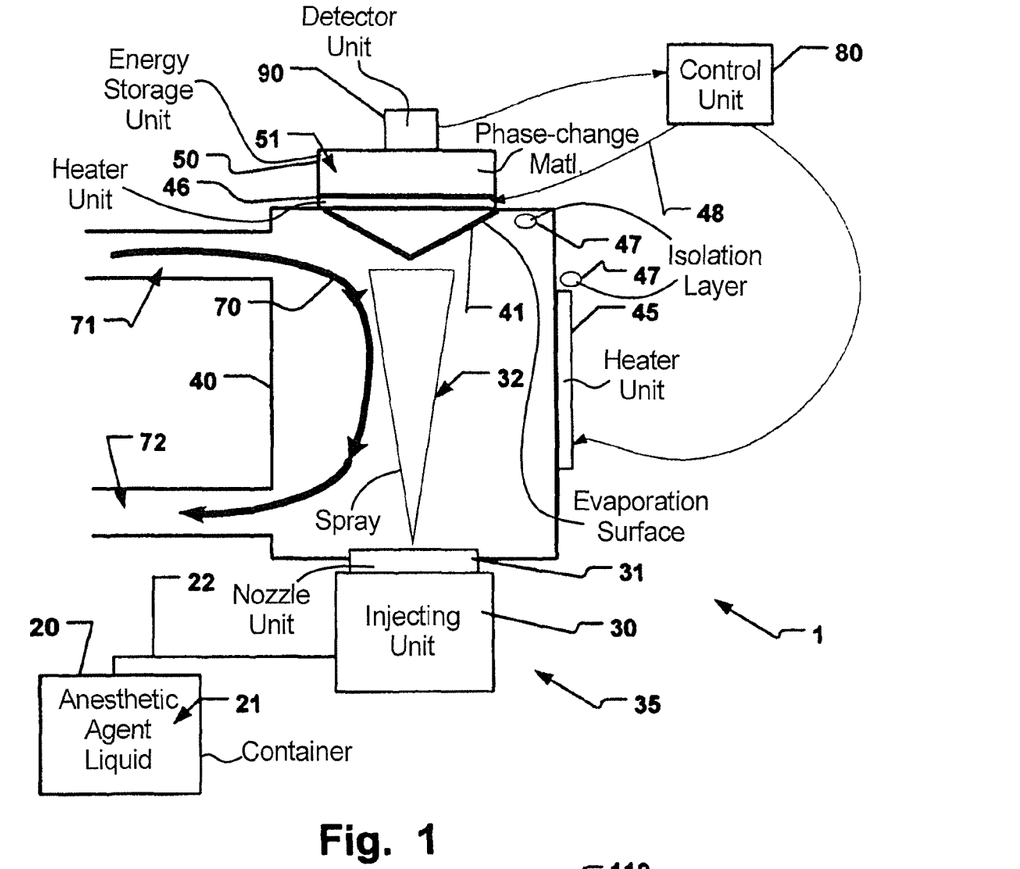
Figure 4:
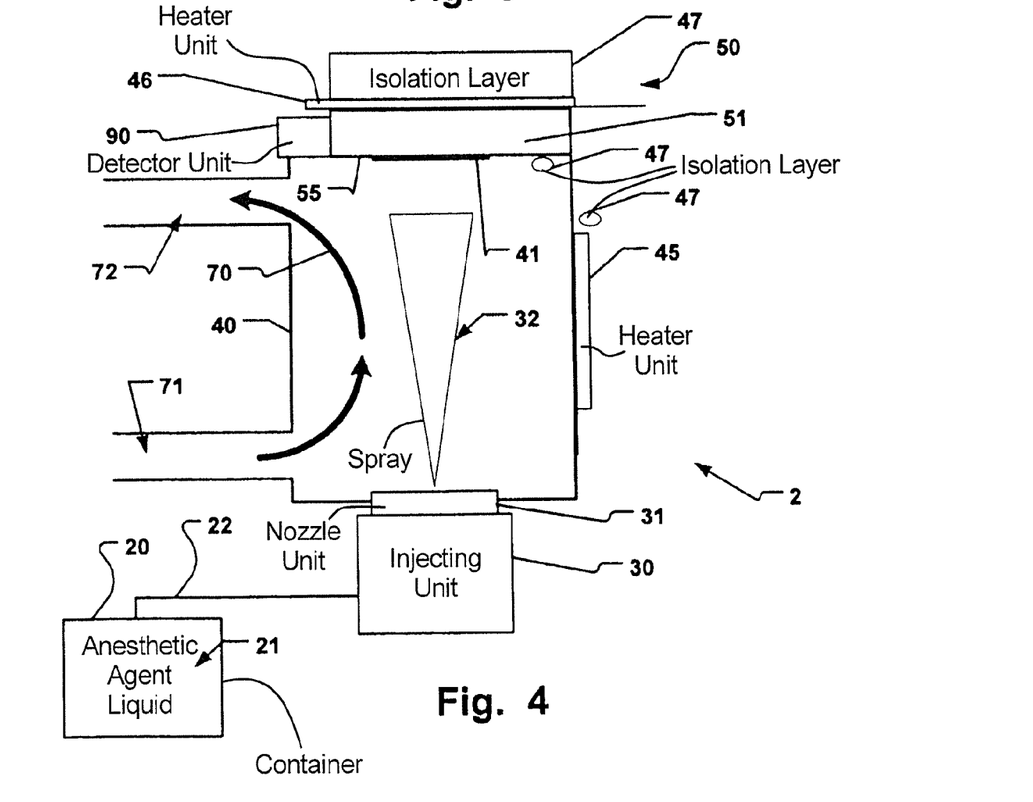

In some embodiments, the method comprises generating a pulsed, intermittent spray of the liquid into the vaporization chamber. The spray may be directed towards the evaporation surface portion. The spray may, also land on the evaporation surface after bouncing or dripping off first target surfaces of the spray. This is made for evaporating the injected liquid at least partly from the evaporation surface when (finally) landing thereon. The method further comprises providing heat energy from a heat energy storage unit comprising a melted phase change material (PCM). The heat energy storage unit, or at least a unit comprising the PCM thereof, is thermally coupled to at least a portion of the evaporation surface on which the anesthetic agent liquid lands from a portion of the spray that has not gasified on its flight to the surface. The liquid may also pass several surfaces before landing on the evaporation surface. The PCM has a phase shift temperature that is higher than the evaporation temperature of the anesthetic agent. Thus the method further comprises keeping the PCM in the heat energy storage unit at least partly liquid at an operative temperature of the vaporizer. Temperature at an evaporation surface is stabilized at a level above the evaporation temperature of the liquid.

Further embodiments of the invention are defined in the dependent claims, wherein features for the second and subsequent aspects of the invention are as for the first aspect mutatis mutandis.

Some embodiments of the invention provide for more heat energy being provideable momentarily for evaporation, compared to heating units dimensioned for a medium temperature of the vaporizer chamber. A lower mean power may be provided to a heater unit than necessary for maintaining a vaporization chamber of a vaporizer, such as an injection vaporizer, at an operational temperature. Peak heat energy needed during vaporization of the spray is provided by the PCM. Thus, vaporization is provided in an energy efficient manner. Accumulation of liquid, such as in pools in the vaporization chamber, is effectively avoided. AS the PCM is locally arranged at the evaporation surface only, a relatively small volume of PCM needed compared to a PCM arranged to keep an entire reservoir of liquid at a desired temperature (which moreover would be below the evaporation temperature of the liquid to avoid unintentional or uncontrolled evaporation of the liquid, contrary to the present embodiments). The reservoir may now even be located remotely from the evaporation chamber of the vaporizer.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1 is a schematic illustration of an embodiment of an injection vaporizer;

FIG. 2 is a graph illustrating a change of temperature at an evaporation surface of an embodied injection vaporizer during operation thereof in comparison to a conventional injection vaporizer;

FIG. 3 is a graph illustrating the temperature development during solidification of the PCM in relation to the pulse time;

FIG. 4 is a schematic illustration of another embodiment of an injection vaporizer;

FIG. 5 is a schematic illustration of a breathing apparatus;

FIG. 6 is a flowchart of a method;

FIG. 7 is a schematic illustration of a further embodiment of an injection vaporizer; and FIG. 8 is a schematic illustration of yet a further example of an injection vaporizer implemented with PCM.

DESCRIPTION OF THE PREFERRED EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

In an embodiment of the invention according to FIG. 1, an anesthetic vaporizer in form of an injection vaporizer 1 is provided. The injection vaporizer 1 is arranged for vaporizing an anesthetic agent liquid 21. The injection vaporizer 1 comprises an interior evaporation surface portion 41. The interior surface portion 41 is usually arranged inside the injection vaporizer, such as in the vaporizer chamber 40. The anesthetic liquid is stored remote from the chamber 40, e.g. in a container or vessel 20. The vessel 20 is in fluid communication with an evaporation unit 35 including an injecting unit 30. The injection unit 30 is provided for generating a pulsed, intermittent spray 32 of the liquid. The spray usually comprises droplets of the liquid injected into the chamber 40. The spray 32, e.g. injected from a nozzle unit 31, travels towards the evaporation surface portion 41, as shown in FIG. 1 or 4. The evaporation surface 41 may be flat. In the illustrated embodiment, the evaporation surface 41 receiving the spray 32 has a conical form, which has some advantages as described further below. The injected liquid will thus at least partly land on the evaporation surface 41. A portion of the spray may be gasified in the chamber 40 on its travel towards the evaporation surface 41. When landing on the evaporation surface 41, the liquid shall evaporate from the latter before the next pulse 101 arrives on the evaporation surface 41. This advantageous evaporation is facilitated by the temperature stabilization provided for by present embodiments.

Figure 2:
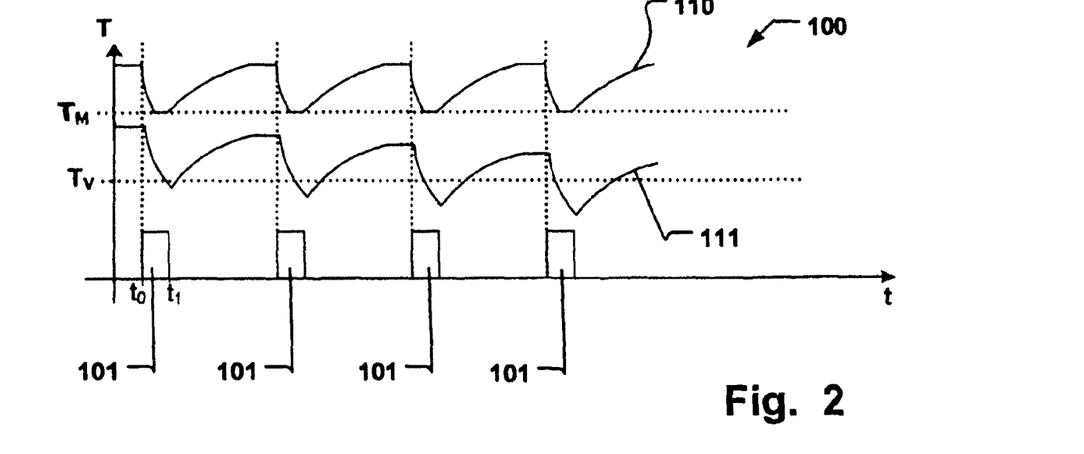

A heat energy storage unit 50 is provided. The unit 50 comprises a phase change material (PCM) 51. The heat energy storage unit 50 is thermally coupled to at least a portion of the evaporation surface 41. The PCM 51 has a solidification temperature (when heat energy is removed from the PCM at dropping temperature direction rightwards in FIG. 3), which also is melting temperature $T_M$ (when heat energy is added to the PCM at increasing temperature direction "leftwards" in FIG. 3) having a plateau phase at the phase shift that is higher than the evaporation temperature $T_V$ of the anesthetic agent, which is illustrated in FIG. 2. In this manner the PCM is at least partly liquid at an operative temperature of the injection vaporizer 1. The operative temperature means the temperature in the vaporizer chamber 40, which is above the evaporation temperature $T_V$ of the anesthetic agent. In particular, in a range between a working temperature $T_W$ and a maximum operation temperature $T_{MAX}$.

The approximate evaporation temperatures, or the boiling point, are for some inhalational anesthetic agents (at sea level) as follows: Desflurane 22.8° C., Isoflurane 48.5° C.; Halothane 50.2° C.; Enflurane 56.5° C.; and Sevoflurane 58.5° C. Resulting operative temperatures, working temperatures $T_W$ and maximum operation temperatures $T_{MAX}$ are above the aforementioned evaporation temperatures temperature $T_V$ of the specific anesthetic agent, respectively. The skilled person will be able to choose suitable phase changing materials, as well as approximate appropriate values for the operative temperatures $T_W$ and $T_{MAX}$ from reading the present specification.

As the liquid volatile agents, in particular with high oxygen concentrations, should be kept below their evaporation temperature (boiling point) before evaporation, a large amount of energy can be saved by the present embodiments. The liquid can be kept at a sufficient cool temperature below the respective evaporation temperature before being injected.

The mass of the PCM (unit) provided is dimensioned such that sufficient heat energy is deliverable for desired pulses 101. The mass is chosen to be sufficiently large or over a critical mass, such to ensure that not the entire volume or mass of the PCM solidifies when providing the evaporation heat to the liquid at the surface 41. However, the mass is very small compared to a mass that would be needed for the entire volume of liquid stored in container 20.

The energy storage unit 50 is thus arranged for providing heat energy for compensation of evaporation heat withdrawn from the evaporation surface by the liquid anesthetic agent when evaporating therefrom.

In this manner, it is ensured that the temperature will not drop under the phase shift temperature $T_M$ of the PCM and thus will be above the evaporation temperature $T_V$ of the anesthetic agent. Thus it is avoided that the entire PCM solidifies at operation of the injection vaporizer, and the temperature of the evaporation surface will locally in the injection vaporizer 1 not drop below the phase shift temperature $T_M$ of the PCM or the evaporation temperature $T_V$. The temperature of the evaporation surface is thus stabilized at an operative temperature of the injection vaporizer. This operation is illustrated in more detail by referring to FIGS. 2 and 3.

FIG. 2 is a graph 100 illustrating a change of temperature at an evaporation surface 41 of an embodied injection vaporizer (curve 110) during operation thereof in comparison to a conventional injection vaporizer (curve 111). Curve 111 is shown below the curve 110 for illustrative purposes, but it will be understood that the lower temperature range of curve 111 may be present after a certain operation time of a conventional injection vaporizer.

As can be seen, the temperature of the evaporation surface 41 does neither drop below the phase shift temperature $T_M$ of the PCM nor the evaporation temperature $T_V$, which is below the phase shift temperature $T_M$. Upon injection of a pulse 101 of the anesthetic agent liquid by means of the injection unit 30, having a time from pulse start time $t_0$ to a pulse end time $t_1$, the temperature T drops over time t and levels out at the phase shift temperature $T_M$. This is due to the phase change occurring at portions of the PCM volume. As the entire PCM volume is not solidified at pulse end time $t_1$, the temperature of the evaporation surface 41 raises again as the heater unit 46 introduces again heat energy. Before reaching the next pulse 101, the temperature has risen back to the initial level. Thus the mean temperature does not drop—it is stabilized by embodiments.

In contrast, it can be seen that the mean temperature of the evaporation surface 41 as shown by curve 101 is constantly decreasing over time, from pulse to pulse. A heater unit not being able to provide sufficient power, and/or a slow temperature regulation leads to the temperature T of the evaporation surface 41 to slowly but steadily fall below the evaporation temperature $T_V$, which has the aforementioned adverse effects.

Figure 3:
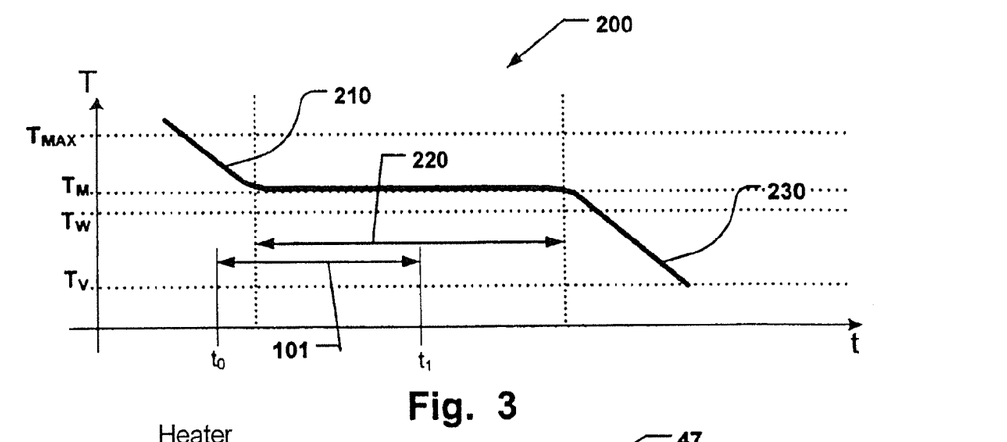

FIG. 3 is a graph 200 illustrating the temperature development during solidification of the PCM. The PCM is in thermal contact with the evaporation surface and it is herein assumed that the temperature of the latter is the same as that of the PCM. The temperature of the PCM drops when heat energy is dissipated from the PCM, as illustrated by region 210. Heat energy may be taken from the PCM from a liquid that changes its physical phase from liquid to gaseous, e.g. when an anesthetic agent liquid evaporated from a surface in thermal contact with the PCM. Before reaching the plateau phase 220, the entire PCM volume is liquid. In the plateau phase 220 the temperature of the PCM is constant during ongoing solidification of the PCM. When the entire PCM is solidified, the temperature will drop further, as shown in section 230. A pulse 101 of the anesthetic agent liquid is shown in the graph 200 for illustrative purposes time from pulse start time $t_0$ to pulse end time $t_1$. It can be seen that the temperature of the PCM does not drop below the phase change (e.g. melting or solidification as explained herein) temperature $T_M$ before the end of the pulse at time $t_1$.

In this manner, it is provided that more heat energy is provideable momentarily for evaporation, at least compared to heating units dimensioned for a medium temperature of the vaporizer chamber, when the portion of the spray 32 has landed on the surface 41. A lower mean power may be provided to a heater unit than necessary for maintaining a vaporization chamber of an injection vaporizer at an operational temperature. Peak heat energy needed during vaporization of the spray is provided by the PCM. Thus, vaporization is provided in an energy efficient manner. Accumulation of liquid, such as in pools in the vaporization chamber, is effectively avoided.

A gas flow 70 passing the injection vaporizer 1, e.g. through inlet 71 and outlet 72, is thus efficiently and reliable enriched with a desired concentration or amount of the gaseous anesthetic agent. The gas flow channel includes for instance a vaporizer chamber 40. The evaporation surface 41 is arranged in the gas channel, here the vaporizer chamber 41, as an interior surface portion thereof.

The heat energy storage unit 50 is in embodiments arranged locally at the evaporation surface. It may be arranged outside of the vaporization chamber 40. Alternatively, it may be arranged at least partly inside the vaporization chamber 40, like inside the conical portion comprising the surface 41 shown in FIG. 1.

Alternatively, or in addition, it is arranged remote from the evaporation surface, but in thermal contact with the latter. This is feasible as not the entire injection vaporizer has to be temperature stabilized, except for locally at a small volume relative the entire volume of the injection vaporizer. The PCM of embodiments is not in thermal contact with the container in which the anesthetic agent is stored prior to generating the spray 32.

Figure 7:
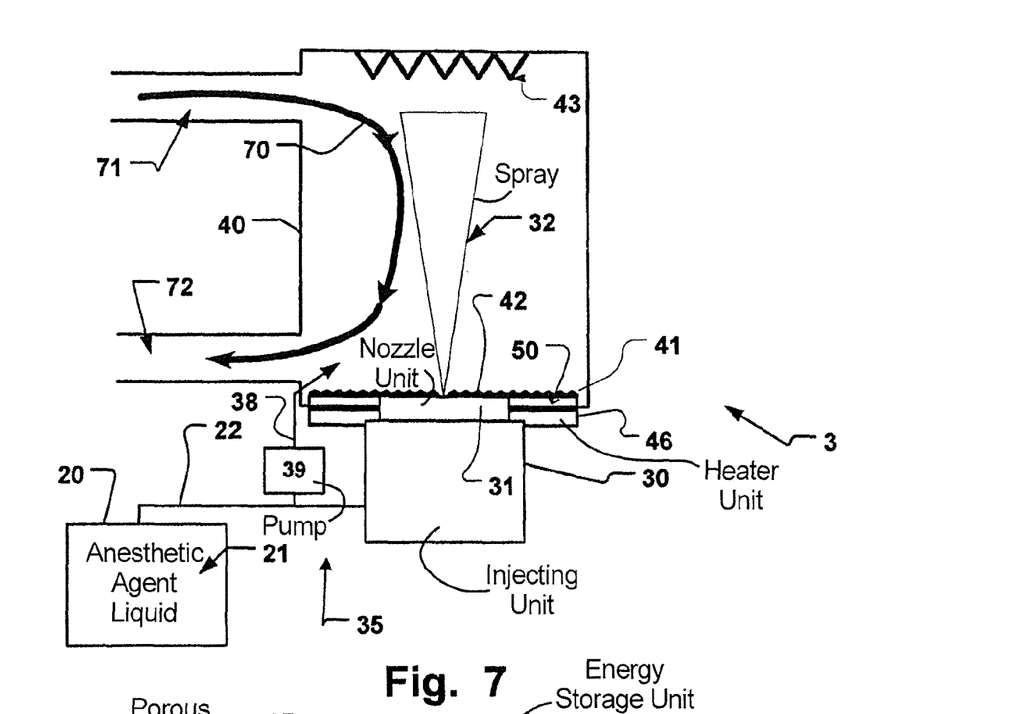

The evaporation surface 41 may comprise an enlarged surface area (such as shown by the enlarged surface area 42 in FIG. 7). The enlarged surface area may comprise one or more conical portion(s) 41 of the interior surface of the gas channel into which the spray 32 is generated, such as shown in FIG. 1. The surface of the cone 41 may in addition be enlarged by the secondary enlarged surface area 42. The enlarged surface area of evaporation surface 41 may for this purpose be corrugated or porous. The enlarged surface area of evaporation surface 41 allows for an increased spreading of the liquid to a larger surface area.

The heat energy storage 50 unit may comprise a carrier unit (not shown) for the PCM. The carrier unit may has an enlarged surface, such as a corrugated or porous surface to increase the available surface for storing PCM or increasing heat transfer surface).

The term "enlarged" in the present context of enlarged surfaces means larger than a flat and/or smooth surface.

An enlarged surface provides for an increased heat exchange surface for improved efficiency.

The porous carrier unit for the PCM may be a sintered porous unit, such as commercially available under the name "sica fil". The porous carrier may alternatively be of aluminum foam. The carrier may have a desired shape and dimension. The porous carrier may be produced by a stabilized aluminum foaming process where air is bubbled through liquid aluminum which in turn is solidified into the desired shape.

The porous carrier unit is preferably of electrically conductive material. An electrically conductive carrier unit is arranged electrically isolated from surrounding units, but thermally in contact with the evaporation surface. In this manner, the heat energy storage unit 50 may have a heating unit integrated into the carrier unit. An electrical current conducted through the carrier unit heats the carrier unit, the PCM, and thus the evaporation surface.

The PCM is separated from the liquid anesthetic agent by a heat conducting separation unit, such as a foil, such as a metal foil, such as an Al foil, wherein the PCM is optionally enclosed by the foil. Thus a compact heat energy storage unit 50 is formed with good heat transfer and no chemical interaction with the agent substance.

A further embodiment of an injection vaporizer 2 is illustrated in FIG. 4. The injection vaporizer has a non-conical evaporation surface 41. Further, the injection vaporizer 2 comprises a heat energy storage unit 50 that has multiple layers including an isolation layer 47, a heater unit layer 46 in thermal contact with the PCM 51, a layer of the PCM 51, and a separation unit layer 55. In this manner, heat from the heater unit 46 is directed towards the PCM layer and thus towards the evaporation surface 41. This sandwich construction providing directed heating isolates the vaporizer chamber to the outside. A compact integrated unit that is easy to manufacture is provided.

The heater unit may in embodiments be a heat film arranged at the PCM, providing a compact unit.

The PCM may be positioned inside the vaporizer chamber as a compact unit, as mentioned above.

The heat energy storage unit 50 may thus be arranged as a lining of a gas channel, such as vaporizer chamber 41 of the injection vaporizer.

The heat energy storage unit 50 is a compact unit. It may have in some embodiments a PCM volume in the range of 10 ml to 100 ml, without being restricted to this volume range. The heat energy storage unit 50 has thus a small size and weight, allowing for a compact injection vaporizer. The volume of the PCM is chosen to be sufficient for injection vaporizer applications, at least at average or expected fresh gas flows, or a fresh gas flow range adjustable in a breathing apparatus comprising the injection vaporizer.

The injection vaporizer 1, 2 comprises a temperature measuring unit for directly or indirectly measuring a temperature of the PCM. The temperature measuring unit may comprise a detector unit 90 for measuring a phase or phase shift of the PCM and for providing a temperature signal indicative of the temperature based on the measured phase or phase shift. Indirect measurements may for instance be based on capacitive or optical detection principles. Alternatively, or in addition, one or more temperature sensors 47 may be provided accordingly.

An additional heater unit 45 may be provided for controlling the mean temperature of the vaporization chamber 40.

The injection vaporizer may comprising a control unit 80 adapted to process the temperature signal for controlling an evaporation process of the anesthetic agent at the evaporation surface 41. The control unit 80 may be adapted to activate a heater unit 46 when the signal is indicative of a solid PCM or a phase shift from liquid PCM to solid PCM. The signal indicative of a measured or detected phase or phase shift of the PCM may be directly based on a temperature of the PCM. The control unit 80 is adapted to control the evaporation process.

In case a complete solidification of the PCM is detected measures may be taken, such as activating an alarm, temporarily reducing the amount of injected anesthetic agent liquid, etc. The heater unit 46 is activated to re-liquefy the PCM in case the temperature thereof is detected to drop under an evaporation temperature of the anesthetic agent or the operating temperature to re-liquefy the PCM.

As shown in FIG. 1, the injection unit 30 may be arranged to generate the spray 32 in a direction opposite that of a flow 70 of gas in the vaporization chamber 40. This further increases efficiency of the injection vaporizer, as less liquid reaches the evaporation surface, because a larger portion of liquid can be evaporated on the flight of the droplets in the vaporization chamber 40.

Examples for PCM materials to be comprised or useful in implementations of embodiments are given hereinafter. Suitable PCM materials may comprise amongst others, salt based compounds, such as salt Hydrates; organic compounds; clathrates, singly or in combination. Some examples are given hereinafter, without being limited to these, wherein the respective phase shift (melting or solidification) temperature is given in parenthesis: $MgCl_2.6H_2O$ (117° C.); $Mg(NO_3)_2.6H_2O$ (89° C.); $CH3COONa.3H2O$ (58° C.); $Mg(NO_3)2.6H_2O/Mg(NO_3)_2.6H_2O$ (58° C.); $Na_2HPO_4.12H_2O$(34° C.). Another example of a suitable PCM is a mixture of Sodium Acetate and Water. For instance, materials are commercially available from Climator AB, Sweden. An example is their material ClimSel C58 that has a phase transition from solid to liquid (or vice versa) at 58° C. Phase shift as useful implementable in embodiments includes a shift from liquid to solid, gaseous to liquid, gaseous to solid where heat energy can be delivered from the PCM to a surrounding environment. Preferably, the phase shift is from the liquid state to the solid state of the PCM.

A PCM may be used having an adjustable phase shift temperature for using the vaporizer with different anesthetic agents. The phase shift temperature may be adjusted depending on the desired anesthetic agent's evaporation temperature.

Alternatively, or in addition, the heat energy storage unit 50 may be exchangeable for using the vaporizer 1 with different anesthetic agents.

Modular heat energy storage units 50 may be provided.

The modules may be exchangeable.

A PCM unit may be provided exchangeable.

Different modules may have different effect power of a heater unit and a different PCM depending on the vaporization temperature needed for a specific anesthetic agent liquid.

FIG. 7 is a schematic illustration of a further embodiment of an anesthetic vaporizer 3. A plurality of conical elements 41 is arranged at a top inner surface of the vaporizing chamber. The cones 41 may receive the injected liquid, which in turn drips down to the upside-down tip of at least some cones of the plurality of cones 43. The liquid then drips from the top down in the vaporizing chamber 40 to the bottom surface thereof. Alternative surface forms to the cones may be provided, such as pins or other units having a drop edge. At the bottom surface of the vaporizing chamber 40, a heat energy storage unit 50 is arranged with a PCM unit and a heater unit 46. The latter may be arranged around the nozzle unit 31. Alternatively, or in addition, these units may be integrated singly or in combination into the injector unit 30 at the bottom of the vaporizing chamber.

Figure 8:
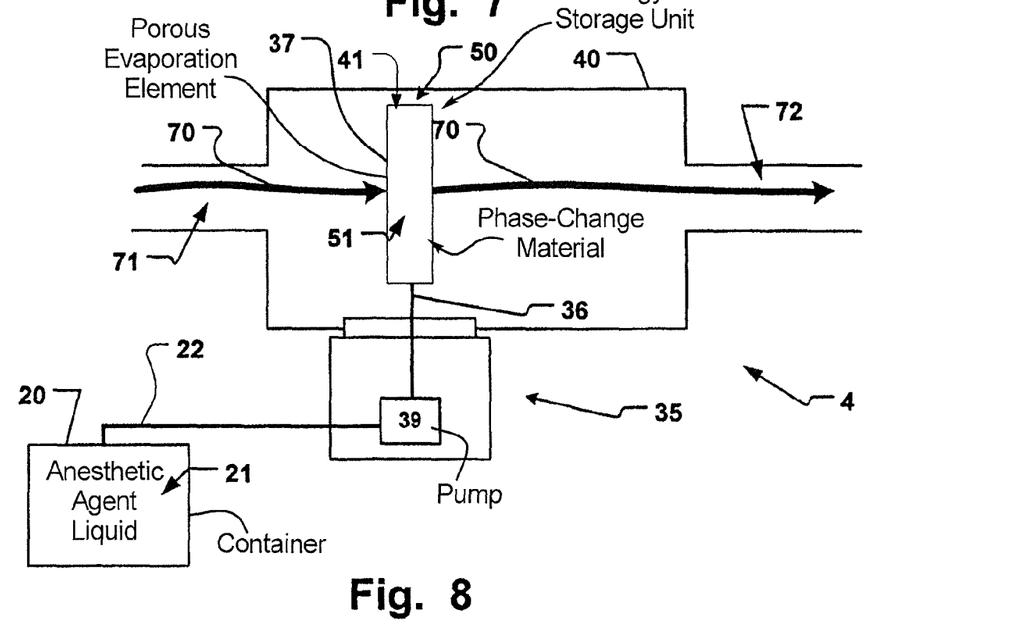

Some of the units shown in FIGS. 1 and 4, such as the temperature measurement units or further heater units, are omitted for illustrative purposes but may be present in the embodiments shown in FIG. 7 or 8.

A fluid line 38 may provide liquid into the vaporization chamber without injection thereof. A pump 39, such as a micropump, may provide for the conveying of the liquid into the vaporizing chamber 40 from the vessel 20. The pump 39 is provided for dosing desired volumes of anesthetic liquid for evaporation into the vaporization chamber. The pump is operated intermittently. The enlarged surface area 42 may be provided at the evaporation surface 41.

The anesthetic vaporizer may have the liquid delivery unit including a pump 39 singly, or in combination with other delivery units, such as an injection unit 31, as shown in FIG. 7.

FIG. 8 is a schematic illustration of yet a further example of an injection vaporizer 4 implemented with PCM. An evaporation unit 35 is provided for evaporating the liquid anesthetic agent 21. Here, a through flow 70 of gas to be enriched with the anesthetic agent is provided through the vaporizer chamber 40. The through flow 70 passes over a porous evaporation element 37. The liquid anesthetic agent is pumped, by means of pump 39, such as a micropump, via a liquid conveying portion of a communication line 36 to the evaporation element 37. A heater may be integrated into the porous element 37 as explained above for porous carrier units. The heater may be operated electrically via an electric connection in communication line 36. The evaporation unit 35 comprises a delivery unit for intermittently adding a volume of the liquid to the evaporation unit for evaporating at least a portion of the volume of the liquid from the evaporation unit 35. The delivery unit may include a pump. The porous evaporation element 37 comprises the PCM 51. The PCM 51 may be arranged at the element 37. Alternatively, or in addition, it may be integrated with the element 37. The PCM material may for instance be brought into porous cavities. Alternatively, or in addition, the PCM may be provided in one or more PCM units carried by element 37 and in thermal contact therewith. Anesthetic agent liquid 21 is intermittently conveyed from the vessel 20 through line 36 to the element 37, comparable to the pulses of injected spray 32. The PCM in the element 37 provides for the temperature stabilization described above.

Various different arrangements of one or more of the heat energy storage units described herein may be made in variations of injection vaporizers 1, 2, 3, 4 by the skilled person when reading the present disclosure. The injection unit 30 may also be arranged at other locations than the bottom, e.g. the top or in lateral positions. A through flow of gas may be provided in some vaporizer chambers. In other examples, an amount of anesthetic liquid may be evaporated in a closed chamber that then is released from the chamber.

Figure 5:
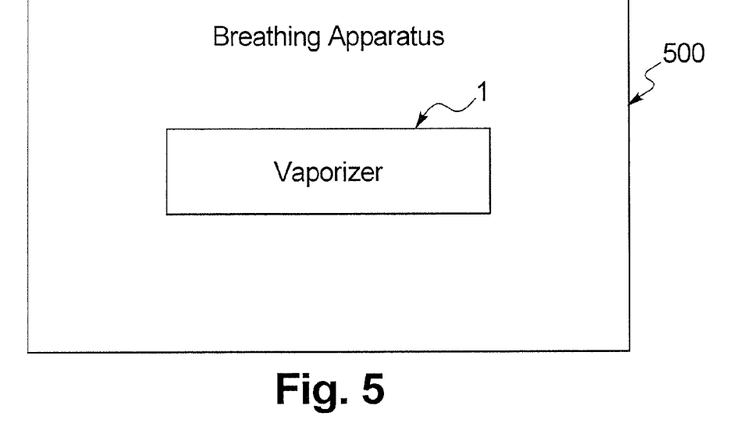

A breathing apparatus 500 comprising an vaporizer is shown in FIG. 5. The apparatus may comprises one or more of anesthetic vaporizers, such as injections vaporizers of embodiments described herein.

Figure 6:
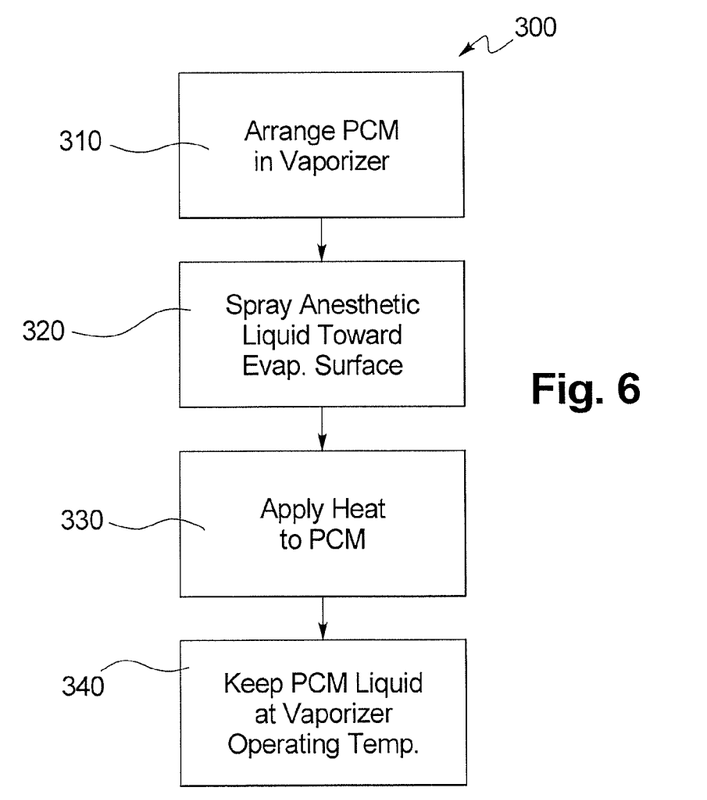

FIG. 6 is a flowchart of a method 300. The method is a method for improving for vaporizing an anesthetic agent liquid in an anesthetic vaporizer, such as an injection vaporizer. The method 300 comprises arranging 310 a PCM in the vaporizer; generating 320 a pulsed, intermittent spray of the liquid towards an evaporation surface portion for evaporating the injected liquid at least partly from the evaporation surface when landing thereon. Furthermore, the method 300 comprises providing 330 heat energy from a heat energy storage unit comprising a phase change material (PCM), which heat energy storage unit is thermally coupled to at least a portion of the evaporation surface, wherein the PCM has a melting temperature that is higher than the evaporation temperature of the anesthetic agent. Thus the method comprises keeping 340 the PCM in the heat energy storage unit at least partly liquid at an operative temperature of the injection vaporizer.

The method may further comprise stabilizing a temperature of the evaporation surface portion during the evaporation by heat provided by the PCM.

The method may further comprise instantaneously providing heat energy from the PCM to the evaporation surface portion and thus the liquid for continued evaporation upon delivery of the liquid, such as by injection of the spray, into a vaporization chamber of the anesthetic vaporizer.

The method may further comprise storing the liquid in a container arranged remote from a vaporization chamber of the vaporizer. The method may in embodiments comprise conveying the liquid to an injection unit of the injection vaporizer for generating the pulsed, intermittent spray of the liquid.

The method may further comprise directing a heat transfer from a heater unit towards the PCM of the heat energy storage unit, and further to the evaporation surface, such as by means of multiple layers of the heat energy storage unit, including an isolation layer, the heater unit in form of a heater unit layer in thermal contact with the PCM, the PCM in form of a PCM, and a separation unit layer, such that heat from the heater unit is directed towards the PCM layer and thus heat from the PCM layer towards the evaporation surface.

The method may further comprise heating a carrier unit for the PCM, wherein the carrier unit has an enlarged surface, such as a corrugated or porous surface for improved heat transfer. The carrier unit may be a porous carrier unit of electrically conductive material, and is arranged electrically isolated, and the method comprises heating the heat energy storage unit by an electrical current conducted through the carrier unit.

The method may further comprise directly or indirectly measuring a temperature of the PCM, such as by means of a detector unit measuring a phase or phase shift of the PCM, and the method comprises providing a temperature signal indicative of the temperature, such as based on the measured phase or phase shift.

The method may further comprise controlling an evaporation process of the anesthetic agent at the evaporation surface based on the temperature signal, such as activating a heater unit of the heat energy storage unit when the temperature signal is indicative of a solid PCM or a phase shift from liquid PCM to solid PCM in at least a portion of the heat energy storage unit.

The method is preferably implemented in an injection vaporizer of embodiments described herein.

In some embodiments, e.g. the injection vaporizer 4 shown in FIG. 8, the method includes providing a heat energy storage unit comprising a phase change material (PCM). The heat energy storage unit is thermally coupled to at least a portion of an evaporation unit. Further, the method includes intermittently adding a volume of the liquid from a delivery unit to the evaporation unit by pumping an amount of liquid from the vessel 20. At least a portion of the volume of the liquid is evaporated from the evaporation unit.

The present invention has been described above with reference to specific embodiments. However, other embodiments than the above described are equally possible within the scope of the invention. Different method steps than those described above, performing the method by hardware or software, may be provided within the scope of the invention. The different features and steps of the invention may be combined in other combinations than those described. The scope of the invention is only limited by the appended patent claims.

Although modifications and changes may be suggested by those skilled in the art, it is the intention of the inventors to embody within the patent warranted heron all changes and modifications as reasonably and properly come within the scope of their contribution to the art.

The invention claimed is:

1. An anesthesia vaporizer for vaporizing an anesthetic agent liquid, said vaporizer comprising
   an evaporation unit for evaporating an anesthetic agent liquid,
   a delivery unit for intermittently adding a volume of said anesthetic agent liquid to said evaporation unit,
   a heat energy storage unit comprising a phase change material (PCM), said heat energy storage unit being thermally coupled to at least a portion of said evaporation unit, and wherein said PCM changes from a first phase to a second phase as heat energy is applied to the PCM, and has a phase change temperature that is higher than a temperature at which said anesthetic agent liquid evaporates and
   a heater in thermal communication with said heat energy storage unit, said heater applying heat energy to said PCM in said heat energy storage unit to maintain at least a portion of said PCM in said second phase during operation of said vaporizer, and thereby maintaining said at least a portion of said evaporation unit at a temperature above said temperature at which said anesthetic agent liquid evaporates.

2. The vaporizer of claim 1, wherein said PCM in said heat energy storage unit is at least partly liquid at said operative temperature of said vaporizer.

3. The vaporizer of claim 1, wherein said vaporizer is an injection vaporizer, and said delivery unit is an injection unit, and said injection vaporizer comprises a gas flow channel including a vaporizer chamber, wherein said evaporation unit is arranged in said vaporizer chamber as at least a portion of an interior evaporation surface thereof, and said heat energy storage unit comprising said PCM is thermally coupled to said at least a portion of said interior evaporation surface.

4. The vaporizer of claim 3, wherein said injecting unit is configured for generating a pulsed, intermittent spray of said liquid toward said evaporation unit surface portion for evaporating said injected liquid at least said evaporation unit that forms partly from at least a portion of said interior evaporation surface.

5. The vaporizer of claim 3, wherein said heat energy storage unit is arranged locally at said evaporation surface and/or in thermal contact with said evaporation surface only in said injection vaporizer.

6. The vaporizer of claim 3, wherein said evaporation surface comprises an at least partly conical portion.

7. The vaporizer of claim 1, wherein said heat energy storage unit comprises a carrier unit for said PCM, and wherein said carrier unit has a corrugated or porous surface.

8. The vaporizer of claim 7, wherein said carrier unit for said PCM is a sintered porous unit, and
   wherein said porous carrier unit is made of an electrically conductive material, and is arranged electrically isolated, for heating said heat energy storage unit by an electrical current conducted through said carrier unit.

9. The vaporizer of claim 1, wherein said PCM is separated from said liquid anesthetic agent by a heat conducting separation unit.

10. The vaporizer of claim 1, wherein said heat energy storage unit has multiple layers including an isolation layer, a layer of said PCM, and a separation unit layer, such that heat from said heater unit is directed toward said PCM layer and thus toward said evaporation unit.

11. The vaporizer of claim 1, wherein said heat energy storage unit is arranged as a lining of a vaporizer chamber and/or a flow channel of said vaporizer.

12. The vaporizer of claim 1, comprising a detector unit measuring a phase or phase shift of said PCM, for providing a temperature signal indicative of a temperature of said PCM.

13. The vaporizer of claim 12, comprising a control unit adapted to process said temperature signal for controlling an evaporation process of said anesthetic agent at said evaporation surface.

14. The vaporizer of claim 13, wherein said control unit is adapted to activate a heater unit when said signal is indicative of a solid PCM or a phase shift from liquid PCM to solid PCM in at least a portion of said heat energy storage unit.

15. A method of vaporizing an anesthetic agent liquid in a vaporizer, said method comprising:
   placing a heat energy storage unit, comprising a phase change material (PCM), in thermal communication with a vaporization chamber of the vaporizer, said PCM changing from a first phase to a second phase as heat energy is applied to the PCM, and having a phase change temperature that is higher than a temperature at which said anesthetic liquid evaporates, providing a volume of said anesthetic agent liquid from a delivery unit to said evaporation unit in said vaporization chamber, applying heat energy to said PCM to maintain at least a portion of said PCM in said second state during operation of said vaporizer, and thereby stabilizing a temperature of said evaporation unit so as to be above said temperature at which said anesthetic agent liquid evaporates, and evaporating said anesthetic agent liquid in said vaporization chamber with said evaporation unit.

16. A method as claimed in claim 15 comprising forming said heat storage unit of multiple layers, said multiple layers comprising an isolation layer, a separation layer and a layer of said PCM, and forming said heater as a heater layer among said multiple layers, with said heater layer being situated between said isolation layer and said layer of PCM, and with said separation layer being situated between said layer of said PCM and said vaporization chamber.

17. The method of claim 16, comprising keeping said PCM in said heat energy storage unit at least partly in a liquid state at an operative temperature of said vaporizer.

18. The method of claim 16, wherein said vaporizer is an injection vaporizer, and said delivery unit is an injection unit, and said adding a volume of said method comprises injecting a volume of said anesthetic agent liquid into a gas flow channel or a vaporizer chamber comprising said gas flow channel, wherein said evaporation unit is arranged in said vaporizer chamber as at least a portion of an interior evaporation surface, and said heat energy storage unit comprises said PCM thermally coupled to at least a portion of said evaporation surface.

19. The method of claim 18, wherein said injecting comprises injecting a pulsed, intermittent spray of said anesthetic agent liquid towards said evaporation surface portion, and said method comprises evaporating said injected liquid at least partly from said evaporation surface.

20. The method of claim 18, comprising stabilizing a temperature of said evaporation surface portion during said evaporation by heat provided by said PCM.

21. The method of claim 18, comprising instantaneously providing heat energy from said PCM to said evaporation surface portion and thus said liquid for continued evaporation upon injecting said liquid into a vaporization chamber of an injection vaporizer.

22. The method of claim 16, comprising storing said anesthetic agent liquid in a container arranged remote from a vaporization site of said vaporizer, and conveying said anesthetic agent liquid from said container to said evaporation unit for said intermittent adding of liquid.

23. The method of claim 16, comprising heating a carrier unit for said PCM, wherein said carrier unit has a corrugated or porous surface for improved heat transfer.

24. The method of claim 23, wherein said carrier unit comprises a porous surface of electrically conductive material, and is arranged electrically isolated, and said method comprises heating said heat energy storage unit by an electrical current conducted through said carrier unit.

25. The method of claim 16, comprising directly or indirectly measuring a temperature of said PCM, by means of a detector unit measuring a phase or phase shift of said PCM, and said method comprises providing a temperature signal indicative of said temperature, based on said measured phase or phase shift.

26. The method of claim 25, comprising controlling an evaporation process of said anesthetic agent liquid at said evaporation unit based on said temperature signal, by activating a heater unit of said heat energy storage unit when said temperature signal is indicative of a solid PCM or a phase shift from liquid PCM to solid PCM in at least a portion of said heat energy storage unit.

\* \* \* \* \*